(12) United States Patent
Mazur

(10) Patent No.: US 12,194,231 B2
(45) Date of Patent: Jan. 14, 2025

(54) AEROSOL-GENERATING SYSTEM WITH FLUID SENSOR

(71) Applicant: Altria Client Services LLC, Richmond, VA (US)

(72) Inventor: Ben Mazur, Bristol (GB)

(73) Assignee: Altria Client Services LLC, Richmond, VA (US)

( * ) Notice: Subject to any disclaimer, the term of this patent is extended or adjusted under 35 U.S.C. 154(b) by 523 days.

(21) Appl. No.: 15/841,808

(22) Filed: Dec. 14, 2017

(65) Prior Publication Data

US 2018/0168229 A1   Jun. 21, 2018

Related U.S. Application Data

(63) Continuation of application No. PCT/EP2017/079408, filed on Nov. 16, 2017.

(30) Foreign Application Priority Data

Dec. 16, 2016   (EP) ..................................... 16204851

(51) Int. Cl.
*A61M 15/00*   (2006.01)
*A24F 40/10*   (2020.01)
(Continued)

(52) U.S. Cl.
CPC ......... *A61M 15/0065* (2013.01); *A24F 40/48* (2020.01); *A24F 40/51* (2020.01);
(Continued)

(58) Field of Classification Search
CPC ........ A24F 47/008; A24F 50/53; A24F 40/10; A61M 11/042; A61M 15/06;
(Continued)

(56) References Cited

U.S. PATENT DOCUMENTS 5,287,752 A * 2/1994 Den Boer ............... G01F 1/712
   73/861.04
5,866,823 A * 2/1999 Scarpa .................... G01F 1/588
   73/861.16
(Continued)

FOREIGN PATENT DOCUMENTS

DE  102007047415 B3 *  4/2009  .......... A61M 11/041
EP     0957959 A2    11/1999
(Continued)

OTHER PUBLICATIONS

Extended European Search Report dated May 30, 2017 issued in corresponding European Application No. 16204851.6.
(Continued)

*Primary Examiner* — Nathaniel E Wiehe
*Assistant Examiner* — Spencer H. Kirkwood
(74) *Attorney, Agent, or Firm* — Harness, Dickey & Pierce, P.L.C.

(57) ABSTRACT

A vapor-generating system includes a pump having an inlet and an outlet, the inlet configured to be connected to a liquid storage portion. The system includes a fluid channel fluidly connected to the pump and a fluid sensor. The fluid sensor is configured to determine a presence of liquid vapor-forming substrate in the fluid channel based on measuring an electrical property of the fluid in the fluid channel.

11 Claims, 5 Drawing Sheets

(51) Int. Cl.
 *A24F 40/48*  (2020.01)
 *A24F 40/51*  (2020.01)
 *A24F 40/53*  (2020.01)
 *A61M 11/04*  (2006.01)
 *A61M 15/06*  (2006.01)
 *A61M 16/00*  (2006.01)

(52) U.S. Cl.
 CPC ............ *A24F 40/53* (2020.01); *A61M 11/042* (2014.02); *A61M 11/044* (2014.02); *A61M 15/06* (2013.01); *A24F 40/10* (2020.01); *A61M 2016/0015* (2013.01); *A61M 2016/003* (2013.01); *A61M 2205/0216* (2013.01); *A61M 2205/0238* (2013.01); *A61M 2205/18* (2013.01); *A61M 2205/276* (2013.01); *A61M 2205/3317* (2013.01); *A61M 2205/3389* (2013.01); *A61M 2205/50* (2013.01); *A61M 2205/581* (2013.01); *A61M 2205/583* (2013.01)

(58) Field of Classification Search
 CPC .... A61M 2005/276; A61M 2205/3389; A61M 15/0065
 See application file for complete search history.

(56) References Cited

U.S. PATENT DOCUMENTS

| | | | | |
|---|---|---|---|---|
| 7,133,786 | B1* | 11/2006 | Dykesteen | ............ G01F 1/7088 |
| | | | | 702/50 |
| 9,072,321 | B2 | 7/2015 | Liu | |
| 2006/0047368 | A1* | 3/2006 | Maharajh | ................ F22B 37/38 |
| | | | | 128/200.14 |
| 2010/0088812 | A1* | 4/2010 | Chen | ...................... E03D 13/00 |
| | | | | 4/301 |
| 2012/0167906 | A1 | 7/2012 | Gysland | |
| 2012/0318882 | A1 | 12/2012 | Abehasera | |
| 2013/0213418 | A1 | 8/2013 | Tucker et al. | |
| 2015/0173419 | A1* | 6/2015 | Tu | ............ A24F 40/51 |
| | | | | 131/329 |
| 2015/0305410 | A1 | 10/2015 | Liu | |
| 2016/0157523 | A1* | 6/2016 | Liu | ........................ A61M 15/06 |
| | | | | 392/395 |
| 2016/0262451 | A1* | 9/2016 | Liu | .......................... A24F 40/53 |
| 2016/0338407 | A1 | 11/2016 | Kerdemelidis | |
| 2017/0055588 | A1* | 3/2017 | Cameron | .............. A61M 15/06 |
| 2017/0224016 | A1* | 8/2017 | Reevell | ............... H05B 1/0227 |
| 2017/0231278 | A1* | 8/2017 | Mironov | .................. G01F 23/26 |
| | | | | 392/390 |
| 2017/0231282 | A1* | 8/2017 | Bowen | .................... A24F 40/42 |
| | | | | 131/329 |
| 2018/0184722 | A1* | 7/2018 | Murison | ............... F04B 43/046 |
| 2018/0369811 | A1* | 12/2018 | Yossifon | ............. B01L 3/50273 |

FOREIGN PATENT DOCUMENTS

| | | |
|---|---|---|
| EP | 2143346 A1 | 1/2010 |
| GB | 2533653 A | 6/2016 |
| WO | WO-1997/042993 A2 | 11/1997 |
| WO | WO-2014/150552 A1 | 9/2014 |
| WO | WO-2014/153515 A1 | 9/2014 |
| WO | WO-2017/108394 A1 | 6/2017 |
| WO | WO-2017/108429 A1 | 6/2017 |

OTHER PUBLICATIONS

International Search Report and Written Opinion dated Feb. 12, 2018 issued in corresponding International Application No. PCT/EP2017/079408.

* cited by examiner

AEROSOL-GENERATING SYSTEM WITH FLUID SENSOR

CROSS-REFERENCE TO RELATED APPLICATIONS

This application is a continuation of, and claims priority to, international application no. PCT/EP2017/079408, filed on Nov. 16, 2017, and further claims priority under 35 U.S.C. § 119 to European Patent Application No. 16204851.6, filed on Dec. 16, 2016, the entire contents of each of which are incorporated herein by reference.

BACKGROUND

Field

Some example embodiments relate to a vapor-generating system with a pump having an inlet and an outlet, the inlet being connectable to a liquid storage portion and a fluid channel. Some example embodiments relate to a method for generating a vapor.

Description of Related Art

One type of vapor-generating system (also called an aerosol-generating system) comprises a liquid storage portion, a pump and a vaporizer. During a puff of a user ("adult vaper") (e.g., air being drawn through an airflow path of the system by an adult vaper), a stream of liquid vapor-generating substrate (e.g., e-liquid) is actively pumped from the liquid storage portion to the vaporizer by means of the pump. In such a system—when the liquid in the liquid storage portion is used up ("depleted")—the vaporizer may be heated, while no liquid vapor-generating substrate is provided to the vaporizer. As a result, heated air, which does not contain a generated vapor, may be drawn. Drawing heated air only may be unpleasant for the adult vaper and is thus unwanted. Also, heating of the vaporizer or a wicking material when there is no liquid present may result in the release of undesirable products.

It would therefore be desirable to provide an improved vapor-generating system which prevents activation of the system once the liquid vapor-generating substrate in the liquid storage portion is used up.

SUMMARY

According to some example embodiments, a vapor-generating system may include a fluid channel fluidly connected to a liquid source, and a fluid sensor. The fluid sensor may be configured to generate a sensor signal indicating a presence of liquid vapor-forming substrate in the fluid channel based on measuring an electrical property of a fluid in the fluid channel.

The vapor-generating system may further include a dispensing device configured to dispense the liquid vapor-forming substrate, the dispensing device in fluid communication with the liquid source.

The fluid channel and the fluid sensor may be between the liquid source and the dispensing device.

The electrical property may be an electrical resistance of the fluid in the fluid channel.

The fluid sensor may include a first electrode and a second electrode.

The first electrode may be at a first channel wall of the fluid channel, the second electrode may be at a second channel wall of the fluid channel, and the first electrode and the second electrode may be both in direct contact with the fluid in the fluid channel.

The first electrode may be at an opposite channel wall in relation to the second electrode.

The fluid sensor may include a voltage divider circuit.

The sensor signal may indicate a type of fluid based on the electrical property of the fluid in the fluid channel.

The liquid source may include a micropump, a micro stepper motor pump, or a piezoelectric pump.

The vapor-generating system may further include a vaporizer and a controller. The controller may be configured to deactivate the vaporizer based on processing the sensor signal generated by the fluid sensor to determine that no fluid is in the fluid channel or a wrong fluid is in the fluid channel.

The vapor-generating system may further include a main body, the main body including a power supply, wherein the liquid source, the dispensing device, the fluid channel and the fluid sensor are encompassed in the main body, wherein the liquid storage portion is included in a cartridge, the cartridge configured to be releasably connected to the main body.

According to some example embodiments, a method for generating a vapor may include providing a liquid source configured to supply a liquid vapor-forming substrate, fluidly connecting a fluid channel to the liquid source, and coupling a fluid sensor to the fluid channel, such that the fluid sensor is configured to generate a sensor signal indicating a presence of the liquid vapor-forming substrate in the fluid channel based on measuring an electrical property of a fluid in the fluid channel.

The method may further include providing a controller, the controller configured to deactivate a vaporizer based on processing the sensor signal generated by the fluid sensor to determine that no fluid is in the fluid channel, or a wrong fluid is in the fluid channel.

The electrical property may be an electrical resistance of the fluid in the fluid channel.

The fluid sensor may include a first electrode and a second electrode.

The first electrode may be at a first channel wall of the fluid channel, the second electrode may be at a second channel wall of the fluid channel, and the first electrode and the second electrode may be both in direct contact with the fluid in the fluid channel.

The first electrode may be at an opposite channel wall in relation to the second electrode.

The fluid sensor may include a voltage divider circuit.

The sensor signal may indicate a type of fluid based on the electrical property of the fluid in the fluid channel.

BRIEF DESCRIPTION OF THE DRAWINGS

Example embodiments will be further described, by way of example only, with reference to the accompanying drawings in which.

DETAILED DESCRIPTION

Figure 1:
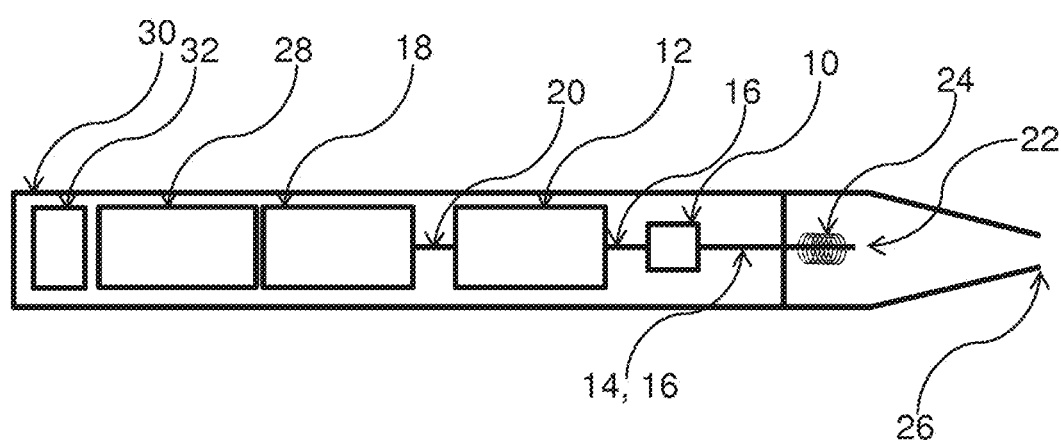
FIG. 1 shows an illustrative cross section of an vapor-generating system according to some example embodiments.

Example embodiments will become more readily understood by reference to the following detailed description of the accompanying drawings. Example embodiments may, however, be embodied in many different forms and should not be construed as being limited to the example embodiments set forth herein. Rather, these example embodiments are provided so that this disclosure will be thorough and complete. Like reference numerals refer to like elements throughout the specification.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises," "comprising," "includes," and/or "including," when used in this specification, specify the presence of stated features, integers, steps, operations, and/or elements, but do not preclude the presence or addition of one or more other features, integers, steps, operations, elements, and/or groups thereof.

It will be understood that when an element or layer is referred to as being "on", "connected to" or "coupled to" another element or layer, it can be directly on, connected or coupled to the other element or layer or intervening elements or layers may be present. In contrast, when an element is referred to as being "directly on", "directly connected to" or "directly coupled to" another element or layer, there are no intervening elements or layers present. As used herein, the term "and/or" includes any and all combinations of one or more of the associated listed items.

It will be understood that, although the terms first, second, etc. may be used herein to describe various elements, regions, layers and/or sections, these elements, regions, layers and/or sections should not be limited by these terms. These terms are only used to distinguish one element, region, layer or section from another region, layer or section. Thus, a first element, region, layer or section discussed below could be termed a second element, region, layer or section without departing from the teachings set forth herein.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

Some example embodiments are described herein with reference to cross-section illustrations that are schematic illustrations of idealized embodiments (and intermediate structures). As such, variations from the shapes of the illustrations as a result, for example, of manufacturing techniques and/or tolerances, are to be expected. Thus, these example embodiments should not be construed as limited to the particular shapes of regions illustrated herein, but are to include deviations in shapes that result, for example, from manufacturing. For example, an implanted region illustrated as a rectangle will, typically, have rounded or curved features and a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of this disclosure.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and this specification and will not be interpreted in an idealized or overly formal sense unless expressly so defined herein.

Unless specifically stated otherwise, or as is apparent from the discussion, terms such as "processing" or "computing" or "calculating" or "determining" or "displaying" or the like, refer to the action and processes of a computer system, or similar electronic computing device, that manipulates and transforms data represented as physical, electronic quantities within the computer system's registers and memories into other data similarly represented as physical quantities within the computer system memories or registers or other such information storage, transmission or display devices.

As disclosed herein, the term "storage medium", "computer readable storage medium" or "non-transitory computer readable storage medium," may represent one or more devices for storing data, including read only memory (ROM), random access memory (RAM), magnetic RAM, core memory, magnetic disk storage mediums, optical storage mediums, flash memory devices and/or other tangible machine readable mediums for storing information. The term "computer-readable medium" may include, but is not limited to, portable or fixed storage devices, optical storage devices, and various other mediums capable of storing, containing or carrying instruction(s) and/or data.

Furthermore, at least some portions of example embodiments may be implemented by hardware, software, firmware, middleware, microcode, hardware description languages, or any combination thereof. When implemented in software, firmware, middleware or microcode, the program code or code segments to perform the necessary tasks may be stored in a machine or computer readable medium such as a computer readable storage medium. When implemented in software, processor(s), processing circuit(s), or processing unit(s) may be programmed to perform the necessary tasks, thereby being transformed into special purpose processor(s) or computer(s).

When the terms "about" or "substantially" are used in this specification in connection with a numerical value, it is intended that the associated numerical value include a tolerance of ±10% around the stated numerical value. The expression "up to" includes amounts of zero to the expressed upper limit and all values therebetween. When ranges are specified, the range includes all values there between such as increments of 0.1%. Moreover, when the words "generally" and "substantially" are used in connection with geometric shapes, it is intended that precision of the geometric shape is not required but that latitude for the shape is within the scope of the disclosure.

According to some example embodiments there is provided a vapor-generating system (also called an aerosol-generating system), comprising a pump having an inlet and an outlet, the inlet being connectable to a liquid storage portion. The pump and liquid storage portion may be referred to herein as collectively comprising a "liquid source." The system also comprises a fluid channel fluidly connected to the pump and a fluid sensor (thereby being fluidly connected to a liquid source). The fluid sensor is configured to generate a sensor signal based on measuring an electrical property of the fluid in the fluid channel. In some example embodiments, the fluid sensor is configured to generate a sensor signal indicating a presence of liquid vapor-forming substrate (also called an aerosol-forming substrate) in the fluid channel, for example based on measuring an electrical property of the fluid in the fluid channel. The sensor signal may be processed (e.g., by a controller as described herein) in order to determine ("detect") the presence of liquid vapor-forming substrate in the fluid channel. Such a determination ("detection") may be understood to be performed by an element performing the processing of the sensor signal (e.g., the controller).

The vapor-generating system of some example embodiments allows ("enables") detection of the presence of liquid vapor-forming substrate in the fluid channel. Beneficially, a vaporizer of the system can be deactivated when the fluid sensor generates a sensor signal that provides an indication that no fluid is present in the fluid channel, thereby enabling a controller to determine ("detect") that no fluid is present in the fluid channel based on processing the sensor signal generated by the fluid sensor. The drawing of only hot air is thus prevented, thereby prohibiting an unpleasant experience for the adult vaper and the generation of undesirable products. The sensor signal, generated by the fluid sensor, indicating that no more liquid vapor-forming substrate is present in the fluid channel, and furthermore the determination that no more liquid vapor-forming substrate is present in the fluid channel based on a processing of the sensor signal, may be utilized to make a determination, and further provide an indication, that a fresh liquid storage portion must be supplied.

The vapor-generating system may further comprise a dispensing device for dispensing ("configured to dispense") the liquid vapor-forming substrate, wherein the dispensing device is in fluid communication with the outlet of the pump. The fluid channel and the fluid sensor may be provided ("located") between the pump and the dispensing device. The fluid sensor may be provided adjacent to the dispensing device, wherein the dispensing device may be provided adjacent to the vaporizer. However, the fluid sensor may be provided anywhere in the system between the liquid storage portion (e.g., the liquid source) and the dispensing device.

If the fluid sensor is provided downstream of the pump between the pump and the dispensing device and/or downstream of the liquid source between the liquid source and the dispensing device, the liquid vapor-forming substrate can be optimally used, since all of the liquid vapor-forming substrate is consumed before the sensor generates a sensor signal that provides an indication that no more liquid is present in the fluid channel. In more detail, even if the liquid in the liquid storage portion is used up, liquid may still be present in the fluid channel. In this case, the system will still operate, until the fluid in the fluid channel downstream of the pump is used up. Thus, the liquid storage portion may be completely depleted of liquid vapor-forming substrate before the fluid sensor generates a sensor signal that provides an indication that no more substrate is present.

The fluid sensor may be configured to measure an electrical property of the fluid comprised in the fluid channel. The electric property measured by the fluid sensor may be the electrical resistance of the fluid comprised in the fluid channel.

Typical fluids in the fluid channel include ambient air or liquid vapor-forming substrate. When the liquid storage portion still comprises liquid vapor-forming substrate and the substrate is pumped towards the dispensing device by the pump, the substrate will be present in the fluid channel. If, however, the liquid storage portion is emptied of substrate, no more substrate will subsequently be pumped through the fluid channel. Thus, ambient air will be present in the fluid channel. The electrical resistance of ambient air is different from the electrical resistance of liquid vapor-forming substrate. Typically, the electrical resistance of ambient air is higher than the electrical resistance of liquid vapor-forming substrate. Thus, by measuring the electrical resistance of the fluid comprised in the fluid channel, the sensor may determine whether air or substrate is present in the fluid channel.

To be configured to measure the electrical resistance of the fluid comprised in the fluid channel, the fluid sensor may comprise ("include") a first electrode and a second electrode.

The resistance between the first electrode and the second electrode may depend on the amount of liquid vapor-forming substrate held ("located") in the liquid channel. For example, the electrical resistance may increase as the amount of liquid vapor-forming substrate held in the fluid channel decreases.

The electrodes may be arranged ("located") at walls of the fluid channel. For example, the first electrode is provided at a first channel wall of the fluid channel and the second electrode is provided at a second channel wall of the fluid channel. The electrodes may be both in direct contact with the fluid comprised in the fluid channel. The first electrode may be disposed opposite to the second electrode. Restated, the first electrode may be at an opposite channel wall in relation to the second electrode. The electrodes may alternatively be arranged in the liquid channel. The first electrode and the second electrode may be arranged at opposite ends of the liquid channel. At least one of the first and second electrodes may be arranged at or in contact with the wall of the liquid channel. The first and second electrodes may be arranged to each partially surround the liquid channel. The first and second electrodes may be arranged concentrically about a common axis of the liquid channel.

The second electrode may substantially follow the path of the first electrode. This may enable the spacing between the first and second electrodes to remain consistent along the length of the first and second electrodes. The second electrode may be arranged substantially parallel to the first electrode.

The electrodes may be any suitable type of electrode. For example, suitable types of electrodes include point electrodes, ring electrodes, plate electrodes or track electrodes. The first electrode and the second electrode may be the same type of electrode. The first electrode and the second electrode may be different types of electrodes.

The electrodes may by any suitable shape. For example, the electrodes may be: square, rectangular, curved, arcuate, annular, spiral or helical. The electrodes may be substantially cylindrical. The electrodes may comprise one or more sections that are substantially linear, non-linear, planar or non-planar. The electrodes may be rigid. This may enable the electrodes to maintain their shape. The electrodes may be flexible. This may enable the electrodes to conform to the shape of the fluid channel.

The electrodes may have a length, a width and a thickness. The length of the electrodes may be substantially greater than the width of the electrodes. In other words, the electrodes may be elongate. The thickness of the electrodes may be substantially less than the length and the width of the electrodes. In other words, the electrodes may be thin. Thin electrodes and elongate electrodes may have a larger surface area to volume ratio. This may improve the sensitivity of measurements.

The electrodes may comprise any suitable material. The electrodes may comprise any suitable electrically conductive material. Suitable electrically conductive materials include metals, alloys, electrically conductive ceramics and electrically conductive polymers. The materials may include gold and platinum. The electrodes may be coated with a passivation layer. The electrodes may comprise or be coated in material that is sufficiently non-reactive so as not to react with or contaminate the liquid vapor-forming substrate. The electrodes may comprise transparent or translucent material.

To be configured to measure the electrical resistance, the fluid sensor may comprise a voltage divider circuit. A voltage divider circuit enables the measurement of ("is configured to measure") the electric resistance between the first and second electrode of the fluid sensor. However, any known method of measuring the resistance of the fluid between the two electrodes may be employed.

The measured electrical property of the fluid may also be the dielectric constant of the fluid. In this regard, the electrodes may constitute a capacitor. The fluid between the electrodes serves—in this case—as a dielectric medium, wherein the dielectric constant of this fluid may be measured by measuring the capacitance of the capacitor or any known method. The dielectric constant of air is different from the dielectric constant of liquid vapor-forming substrate and can be used to distinguish these fluids.

The electric property, for example the electric resistance or dielectric constant of the fluid in the fluid channel may be indicative of the specific fluid (e.g., a "type" of fluid of the fluid in the fluid channel). By determining the electrical resistance of the fluid in the fluid channel, it may be possible to identify the chemistry of the liquid. In this regard, the electrical resistance of the fluid in the fluid channel may depend upon the chemistry of the liquid. Thus, it may be identified whether or not the correct type of liquid is used. For example, different liquid vapor-forming substrates may be used in the system by subsequently providing liquid storage portions with different substrates. These different substrates may have different electric properties, which may be detectable based on processing one or more sensor signals generated by the fluid sensor. The sensor signals generated by the fluid sensor may be processed to not only detect whether or not substrate is present in the fluid channel, but additionally detect what kind of substrate is present in the fluid channel. Beneficially, the system may be operated on basis of the detection of the specific substrate based on processing one or more sensor signals generated by the fluid sensor. For example, the temperature of a vaporizer may be controlled depending on the used substrate. Also, the heating time may be controlled depending on the used substrate.

The dispensing device may be a nozzle or a tubing segment, also referred to as tube. The dispensing device may comprise a tube and a nozzle at the distal end of the tube. The tube may comprise any appropriate material, for example glass, metal, for example stainless steel, or plastics material, for example PEEK. The size of the tube may match that of the pump outlet. For example, the tube may have a diameter of about 1 to 2 millimeters but other sizes are possible. The tube may be connected to the pump outlet via silicon tubing. The tube may be directly connected to the pump outlet.

The dispensing device may be provided to deliver the liquid vapor-forming substrate to a vaporizer. The vaporizer may comprise a heater for heating the supplied amount of liquid vapor-forming substrate. The heater may be any device suitable for heating the liquid vapor-forming substrate and volatilizing at least a part of the liquid vapor-forming substrate in order to form a vapor. The heater may be a heated coil, a heated capillary, a heated mesh or a heated metal plate. For example, the vaporizer may be provided as a heating coil extending—with respect to the dispensing device—in a longitudinal direction of the dispensing device. The diameter of the heating coil may be chosen such that the heating coil can be mounted around the dispensing device. The heating coil may be mounted transverse to the dispensing device. The heating coil may overlap with the nozzle of the dispensing device. In some examples, there may be a distance between the nozzle of the dispensing device and the heating coil. The length of the heating coil may be 2 millimeters to 9 millimeters, including 3 millimeters to 6 millimeters. The diameter of the heating coil may be 1 millimeter to 5 millimeters, for example 2 millimeters to 4 millimeters.

The heater may comprise only a single heating element or a plurality of heating elements. The temperature of the heating element or elements is preferably controlled by electric circuitry (e.g., a controller).

The electric circuitry may comprise a microprocessor, which may be a programmable microprocessor. The microprocessor may be part of a controller. The electric circuitry may comprise further electronic components. The controller may be configured to regulate a supply of power to the vaporizer. Power may be supplied to the vaporizer continuously following activation of the system or may be supplied intermittently, such as on a puff-by-puff ("draw-by-draw") basis. The power may be supplied to the vaporizer in the form of pulses of electrical current. In some example embodiments, the supply of power to the vaporizer is controlled depending upon the measurement of the fluid sensor. The controller may be configured to process one or more sensor signals generated by the fluid sensor. The controller may be configured to make determinations and/or detections based on processing the one or more sensor signals generated by the fluid sensor. When the fluid sensor generates a sensor signal that may be processed (e.g., by a controller as described herein) to determine ("detect") that no more liquid is present in the fluid channel, power supply to the vaporizer may be prohibited by the controller in response to said determining ("detecting"). Additionally or alternatively, the power supply to the vaporizer may be controlled (e.g., by the controller) on basis of ("based on") the type of liquid vapor-forming substrate in the fluid channel. For example, the specific heating regime may be executed on basis of the type of substrate. In another example, the power supply to the vaporizer may be prohibited (e.g., the vaporizer may be deactivated), for example by the controller, based on a sensor signal generated by the fluid sensor being processed (e.g., by the controller) to determine (e.g., such that the controller determines) that no fluid is in the fluid channel or a wrong fluid is in the fluid channel.

To be configured to supply power to the vaporizer, the system may comprise a power supply, typically a battery. In some example embodiments, the power supply may be another form of charge storage device such as a capacitor. The power supply may require recharging and may have a capacity that allows for the storage of enough energy for one or more experiences; for example, the power supply may have sufficient capacity to allow for the continuous generation of vapor for a period of several minutes. In another example, the power supply may have sufficient capacity to allow for a particular (or, alternatively, predetermined) number of puffs ("draws") or discrete activations of the vaporizer. The controller may be connected to the power supply and thus may be configured to control the supply of power from the power supply to the vaporizer, for example based on determinations made by the controller as a result of processing one or more sensor signals generated by the fluid sensor.

The vaporizer may also be a piezoelectric transducer or vibrating membrane.

The pump may be a micro pump. The pump may also be provided as a micro stepper motor pump or a piezoelectric pump.

The pump may be controlled by the controller. The controller may stop the operation of the pump based on a determination, via processing of one or more sensor signals generated by the fluid sensor, that no more liquid vapor-forming substrate is present in the fluid channel. Power may be supplied to the pump by means of the power supply.

The pump and/or the vaporizer may be triggered by a puff detection system ("draw detection system"). In some example embodiments, the pump and/or the vaporizer may be triggered based on adult vaper interaction with an on-off button of the system, held for the duration of air being drawn through an airflow path of the system.

The draw detection system may a sensor, which may be configured as an airflow sensor and may measure the airflow rate. The airflow rate is a parameter characterizing the amount of air that is drawn through the airflow path of the system per time by the adult vaper. The initiation of the draw may be detected based on processing sensor signals generated by the airflow sensor when the airflow exceeds a particular (or, alternatively, predetermined) threshold.

The sensor may be configured to generate an output indicative of a magnitude and direction of the airflow, and the controller may receive the sensor output and determine if the following 'wiping conditions' exist: (1) a direction of the airflow indicates a draw on an outlet of the system (versus air entering the system through the outlet), and (2) a magnitude of the airflow exceeds a threshold value. If these internal conditions are met, the controller may electrically connect the power supply to the pump and/or vaporizer, thereby activating same. In some example embodiments, the sensor may generate an output indicative of a pressure drop within the housing of the system (which is caused by a draw of air entering the system), whereupon the controller activates the vaporizer and/or pump, in response thereto. The sensor may be a sensor as disclosed in "Electronic Smoke Apparatus," U.S. application Ser. No. 14/793,453, filed on Jul. 7, 2015 and published as U.S. Publication No. 2015/0305410, or a sensor as disclosed in "Electronic Smoke," U.S. Pat. No. 9,072,321, issued on Jul. 7, 2015, each of which is hereby incorporated by reference in their entirety into this document.

The liquid storage portion may be adapted for storing ("configured to store") the liquid vapor-forming substrate to be supplied to the dispensing device. The liquid storage portion may be configured as a container or a reservoir for storing the liquid vapor-forming substrate.

In some example embodiments, the liquid storage portion is capable of being coupled to the pump inlet by a respective coupling hermetically sealed against surrounding atmosphere. In some example embodiments, the couplings are configured as self-healing pierceable membranes. The membranes avoid undesired leaking of the liquid vapor-forming substrate stored in the liquid storage portion. To be configured to couple the replaceable liquid storage portion to the pump a respective needle-like hollow tube may be pierced through a respective membrane. When the pump is coupled to the liquid storage portion, the membranes avoid undesired leaking of the liquid vapor-forming substrate and leaking of air from and into the liquid storage portion.

The liquid storage portion may be any suitable shape and size. For example, the liquid storage portion may be substantially cylindrical. The cross-section of the liquid storage portion may, for example, be substantially circular, elliptical, square or rectangular.

The liquid storage portion may be a disposable article replaced once the liquid storage portion is empty or below a minimum volume threshold. The system may output a signal such as an optical or acoustical signal based on a detection (e.g., by the controller based on processing a sensor signal generated by the fluid sensor) that the fluid channel is empty of liquid vapor-forming substrate. The signal may indicate that a new liquid storage portion must be provided to replace the old empty liquid storage portion or that the liquid storage portion needs to be refilled.

The vapor-forming substrate is a substrate capable of releasing volatile compounds that can form a vapor. The volatile compounds may be released by heating the vapor-forming substrate. The vapor-forming substrate may comprise plant-based material. The vapor-forming substrate may comprise tobacco. The vapor-forming substrate may comprise a tobacco-containing material containing volatile tobacco flavor compounds, which are released from the vapor-forming substrate upon heating. The vapor-forming substrate may alternatively comprise a non-tobacco-containing material. The vapor-forming substrate may comprise homogenized plant-based material. The vapor-forming substrate may comprise homogenized tobacco material.

In some example embodiments, a tobacco material may include material from any member of the genus *Nicotiana*. In some example embodiments, the tobacco material includes a blend of two or more different tobacco varieties. Examples of suitable types of tobacco materials that may be used include, but are not limited to, flue-cured tobacco, Burley tobacco, Maryland tobacco, Oriental tobacco, rare tobacco, specialty tobacco, dark tobacco, blends thereof and the like. The tobacco material may be provided in any suitable form, including, but not limited to, tobacco lamina, processed tobacco materials, such as volume expanded or puffed tobacco, processed tobacco stems, such as cut-rolled or cut-puffed stems, reconstituted tobacco materials, blends thereof, and the like. In some example embodiments, the tobacco material is in the form of a substantially dry tobacco mass.

The vapor-generating system may be an electrically operated system. In some example embodiments, the vapor-generating system is portable. The vapor-generating system may have a size comparable to a conventional cigar or cigarette. The system may have a total length between approximately 30 millimeters and approximately 150 millimeters. The system may have an external diameter between approximately 5 millimeters and approximately 30 millimeters.

According to some example embodiments, there is provided a method for generating a vapor. The method comprises the step of providing a pump for pumping liquid vapor-forming substrate, the pump having an inlet and an outlet, the inlet being connectable to a liquid storage portion. A fluid channel is provided fluidly connected to the pump. Furthermore, a fluid sensor is provided, wherein the fluid sensor determines a presence of liquid vapor-forming substrate in the fluid channel.

Features described in relation to one aspect may equally be applied to some example embodiments.

FIG. 1 shows an illustrative cross section of a vapor-generating system according to some example embodiments. The vapor-generating system shown in FIG. 1 comprises a fluid sensor 10. The fluid sensor 10 is arranged between a pump 12 and a dispensing device 14. The fluid sensor 10 is arranged at (e.g., is coupled to, is in fluid communication with, etc.) a fluid channel 16. The fluid sensor 10 may measure the electrical resistance of the fluid in the fluid channel 16. Thereby, the fluid sensor 10 may generate a sensor signal that indicates whether liquid vapor-forming substrate is present in the fluid channel 16. Such a sensor signal may be processed by another element (e.g., a controller as described herein) to enable the other element to make a determination (e.g., "to detect") whether liquid vapor-forming substrate is present in the fluid channel 16.

The pump 12 is configured to pump liquid vapor-forming substrate from a liquid storage portion 18 towards the fluid channel 16 and the fluid sensor 10. The pump 12 is fluidly connected with the liquid storage portion 18 by means of an additional fluid channel 20. Collectively, the pump 12 and the liquid storage portion 18 may be referred to herein as a "liquid source."

After the liquid vapor-forming substrate passes the fluid channel 16 and the fluid sensor 10, the liquid vapor-forming substrate is delivered towards the dispensing device 14. The dispensing device 14 is configured as a tubing segment ending in a nozzle 22. Around the dispensing device 14, a heater 24 is arranged. The heater 24 is configured as a heating coil.

The heater 24 heats the liquid vapor-forming substrate in the dispensing device 14 such that a vapor is delivered from the nozzle 22 towards a mouth end ("outlet end") 26 of the vapor-generating system. The vapor is subsequently drawn to an outlet of the system. The heater 24 is powered by a battery 28.

The fluid sensor 10, pump 12, dispensing device 14, fluid channel 16, nozzle 22, heater 24, outlet end 26 and battery 28 are arranged in a housing 30. The housing 30 confines a main body of the system. The housing 30 also comprises a controller 32. The controller 32 controls the activation of the heater 24. When the fluid sensor 10 generates a sensor signal that indicates that no liquid vapor-forming substrate is present in the fluid channel 16, and the controller 32 processes the sensor signal to determine ("detect") that no liquid vapor-forming substrate is present in the fluid channel 16, the controller 32 will deactivate the heater 24. The controller 32 also controls the pumping action of the pump 12. The controller 32 is part of one or more instances of electric circuity which may also determine the type of fluid in the fluid channel 16 based on processing one or more sensor signals generated by the fluid sensor 10, where the one or more sensor signals indicates a fluid sensor 10-measured electrical property of the fluid in the fluid channel (e.g., on basis of ("based on") the electric resistance of the fluid). The controller 32 may deactivate the heater 24, if an undesired fluid is determined (e.g., by the controller 32 based on processing one or more sensor signals generated by the fluid sensor 10) to be present in the fluid channel 16.

In FIG. 1, the liquid storage portion 18 is also arranged in the housing 30. However, the liquid storage portion 18 may be configured as a separate replaceable cartridge which may be attachable to an inlet of the pump 12.

Figure 2:
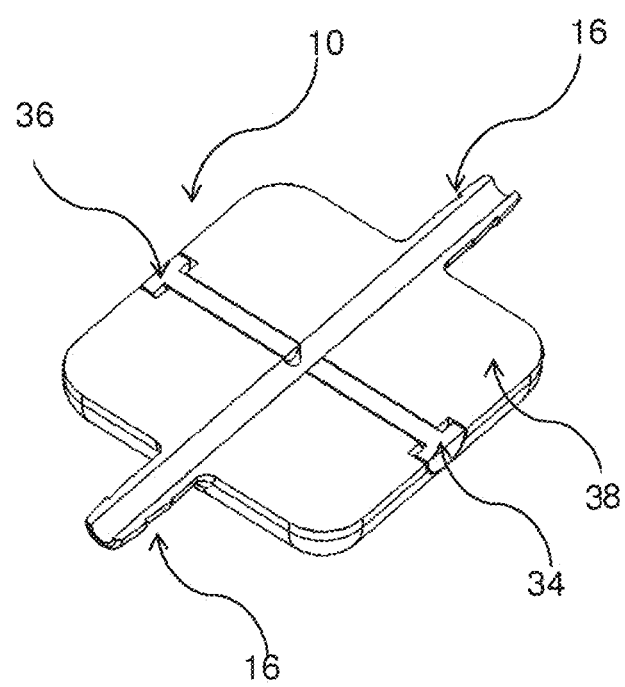
FIG. 2 shows an illustrative cross section of a sensor and a fluid channel according to some example embodiments.

FIG. 2 shows an illustrative cross section of a sensor and a fluid channel according to some example embodiments. FIG. 2 depicts the fluid sensor 10 in more detail. In this regard, FIG. 2 shows the fluid channel 16, wherein a first electrode 34 and a second electrode 36 of the fluid sensor 10 are arranged at the wall of the fluid channel 16.

The first electrode 34 is arranged at the wall of the fluid channel 16 such that the tip of the first electrode 34 is in direct contact with the fluid in the fluid channel 16. The second electrode 36 is arranged on the opposite site of the wall of the fluid channel 16 also in direct contact with the fluid in the fluid channel 16. The first and second electrodes 34, 36 are arranged to measure the electrical resistance of the fluid between the electrodes 34, 36 and thus of the fluid in the fluid channel 16. The electrodes 34, 36 are supported in a carrier 38 for dimensional stability. The fluid sensor 10 has a length and width of 1 millimeter to 1 centimeter and preferably around 3 millimeter. The thickness of the fluid sensor 10 is 0.5 millimeter to 3 millimeter and preferably around 1.5 millimeter. The electrodes have a diameter of 0.9 millimeter. The electrodes have a length of 1 to 5 millimeter and preferably around 3 millimeter. The distance between the electrodes should be as small as possible without impeding the flow of liquid, ideally 1 millimeter or the internal diameter of the tube.

Figure 3:
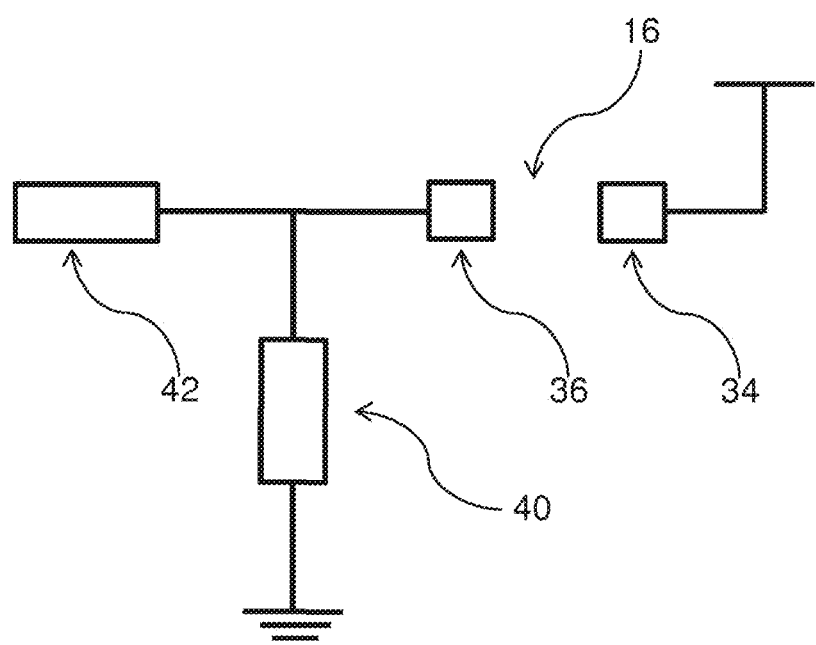
FIG. 3 shows an illustrative wiring diagram of a voltage divider circuit which may be employed in a sensor according to some example embodiments.

FIG. 3 shows an illustrative wiring diagram of a voltage divider circuit which may be employed in a sensor according to some example embodiments. FIG. 3 shows a voltage divider circuit which is used to generate a sensor signal indicating the electrical resistance of the fluid in the fluid channel 16.

In FIG. 3, a voltage divider circuit is modified in that a first resistor is replaced by the first and second electrode 34, 36 and the fluid in the fluid channel 16 between the electrodes 34, 36. Apart thereof, the voltage divider circuit consists of the known elements of a voltage divider circuit. In more detail, a second resistor 40 is provided. The electrical resistance of the second resistor 40 is known. The electrical resistance of the second resistor can be chosen as required and is chosen suitable with respect to the electrical resistance of the liquid vapor-forming substrate. The electrical resistance of the second resistor is chosen in the range of 5 to 20 Megaohm and preferably around 12 Megaohm or approximately equal to the resistance between the two electrodes when liquid is present. Different vapor forming substrates will present different resistances therefore this may need to be specified during the design process. However most resistor values in this range will provide a significant voltage difference when liquid is present vs when it is not. The electrical resistance of the liquid vapor-forming substrate is comparable within different liquid vapor-forming substrates such as e-liquids. A known voltage is applied to the circuit. An analog-to-digital converter 42 is connected to the center tap of the voltage divider circuit. By using the measured voltage, the known electrical resistance of the second resistor 40 and the known applied voltage, the controller 32, which is connected with the analog-to-digital converter 42, computes the electrical resistance of the first resistor. Since the electrical resistance of the electrodes 34, 36 is also known, the controller 32 thus computes the electrical resistance of the fluid in the fluid channel. At the analog-to-digital converter 42, the measured voltage decreases if the electrical resistance of the fluid between the electrodes increases and vice versa.

Figure 4:
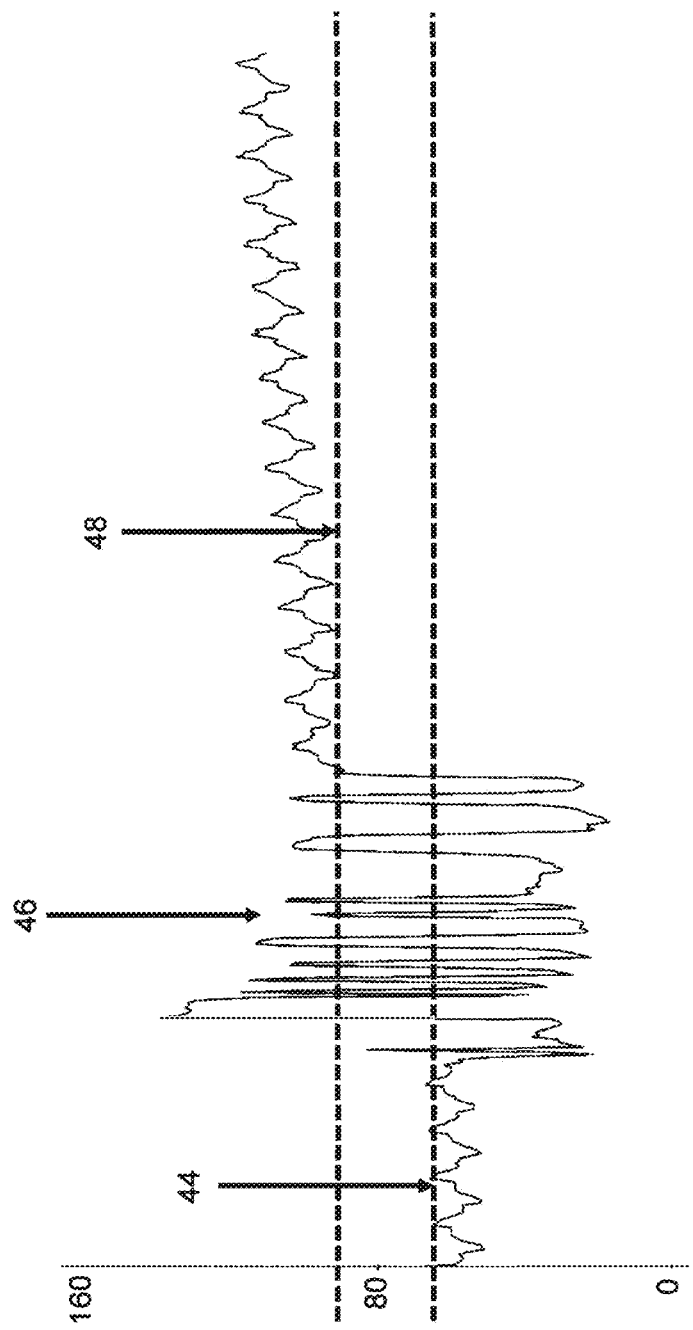
FIG. 4 shows a measurement diagram of a sensor according to some example embodiments.

FIG. 4 shows a measurement diagram of a sensor according to some example embodiments. FIG. 4 shows a measurement of the fluid sensor 10. FIG. 4 depicts the voltage which is measured at the analog-to-digital converter 42. The diagram shows the voltage over time. The electrical resistance of the second resistor 40 was set to 12 Megaohm. At first, no liquid vapor-forming substrate is present in the fluid channel 16. Only air is present in the fluid channel 16. Thus, the measured voltage is low, corresponding to a high electric resistance of the fluid in the fluid channel 16. The electric resistance was determined to be 18 Megaohm when no substrate was present in the fluid channel 16. This measurement is denoted by reference sign 44. Thus, the measurement denoted by reference sign 44 corresponds to a sensor signal, generated by fluid sensor 10, that indicates an absence of fluid in the fluid channel 16, and a controller 32 processing said sensor signal as denoted by reference sign 44 might arrive at the determination that no fluid is present in the fluid channel 16. As shown in FIG. 4, the measured voltage at reference sign 44 may be below one or more particular threshold values (e.g., below one or more of the horizontal dashed lines in FIG. 4). The controller 32 may determine, based on processing the sensor signal corresponding to the measurement denoted by reference sign 44, that the measured voltage is below the one or more particular threshold values and may, as a result, determine that no fluid is present in the fluid channel 16. Before the fluid channel 16 is fully filled with liquid vapor-forming substrate, bubbles emerge, i.e. a mixture of liquid vapor-forming substrate and air. Thus, fluctuating electrical resistance values are determined by the fluid sensor 10. This measurement is denoted by reference sign 46. Thus, the measurement denoted by reference sign 46 corresponds to a sensor signal, generated by fluid sensor 10, that indicates a partial presence of fluid in the fluid channel 16, and a controller 32 processing said sensor signal as denoted by reference sign 46 might arrive at the determination that at least some fluid is present in the fluid channel 16. As shown in FIG. 4, the measured voltage at reference sign 46 may be above one or more particular threshold values and also below one or more other particular threshold values (e.g., extending above and below both of the voltages represented by the horizontal dashed lines in FIG. 4). The controller 32 may determine, based on processing the sensor signal corresponding to the measurement denoted by reference sign 46, that the measured voltage extends below one or more particular threshold values and also above one or more particular threshold values (e.g., one or more other particular threshold values) and may, as a result, determine that at least some fluid is present in the fluid channel 16. When the fluid channel 16 is fully filled with liquid vapor-forming substrate, the measured voltage is high, corresponding to a comparatively low electric resistance of the liquid vapor-forming substrate in the fluid channel 16 (reference sign 48). The electric resistance was determined to be 10 Megaohm when the fluid channel 16 was fully charged with liquid vapor-forming substrate. Thus, the measurement denoted by reference sign 48 corresponds to a sensor signal, generated by fluid sensor 10, that indicates a full presence of fluid in the fluid channel 16, and a controller 32 processing said sensor signal as denoted by reference sign 48 might arrive at the determination that fluid is present in the fluid channel 16. As shown in FIG. 4, the measured voltage at reference sign 48 may be above one or more particular threshold values (e.g., above one or more of the horizontal dashed lines in FIG. 4). The controller 32 may determine, based on processing the sensor signal corresponding to the measurement denoted by reference sign 48, that the measured voltage is above the one or more particular threshold values and may, as a result, determine that fluid is present in the fluid channel 16. The same principle applies when—at first—liquid vapor-forming substrate is present in the fluid channel and—subsequently—air is present in the fluid channel. In this case, liquid vapor-forming substrate will be followed by bubbles and eventually by air.

Figure 5:
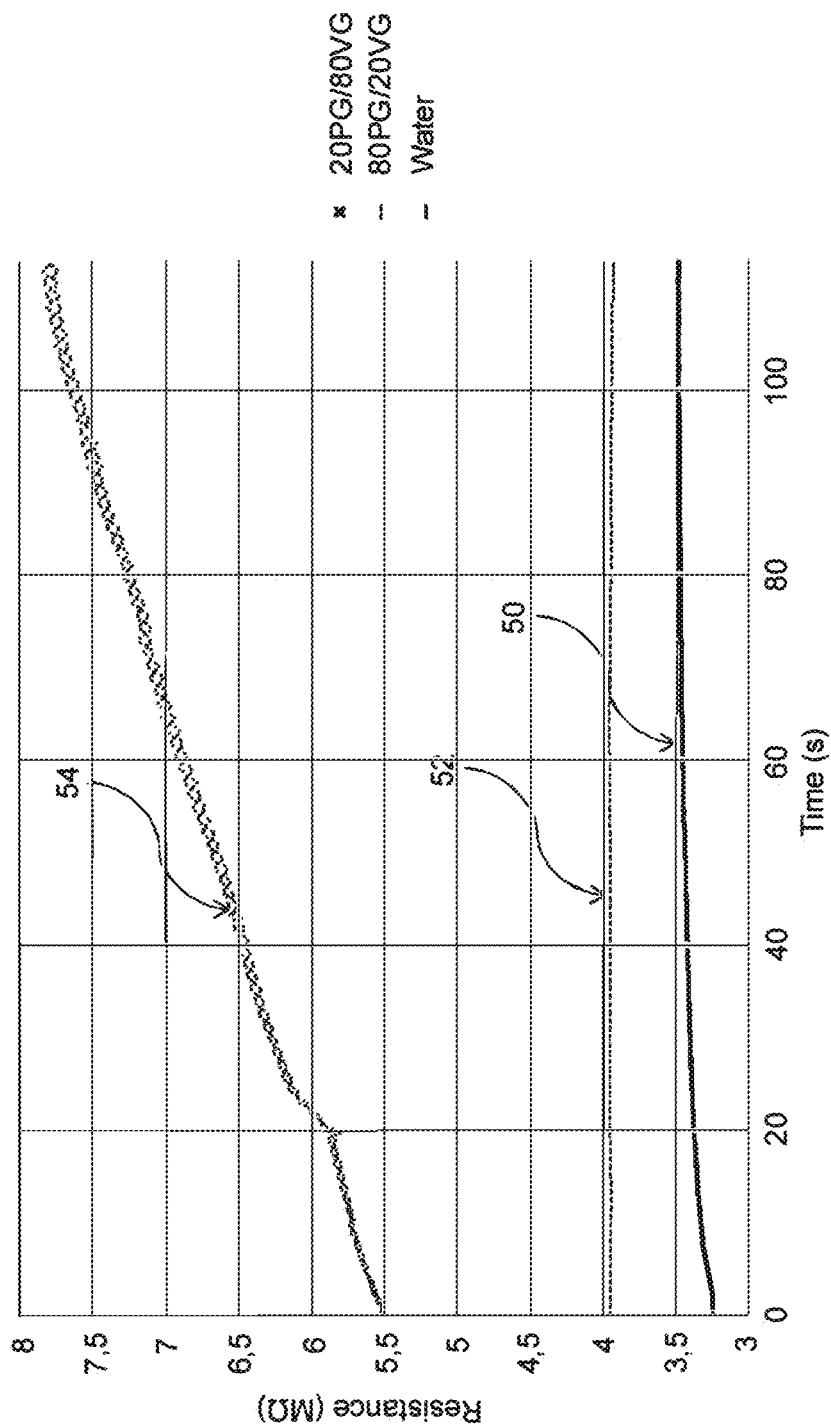
FIG. 5 shows a measurement diagram of a sensor according to some example embodiments.

FIG. 5 shows a measurement diagram of a sensor according to some example embodiments. FIG. 5 is a measurement of the fluid sensor 10 with other parameters than the parameters used in FIG. 4. In the measurement as used in FIG. 5, the electrical resistance of the second resistor 46 was set to 5.6 Megaohm. The measurement shown in FIG. 5 may also be the sensor signal generated by the fluid sensor 10, where the sensor signal indicates the measurement. The measurement was conducted with different fluids in the fluid channel 16. The fluids used were water, a fluid with glycerol, denoted 80 PG/20 VG, and a further fluid with higher glycerol content, denoted 20 PG/80 VG. As shown in FIG. 5, measurements (sensor signals) 50 correspond to measurements of water in the fluid channel 16 by the fluid sensor 10, measurements (sensor signals) 52 correspond to measurements of the fluid with glycerol (80 PG/20 VG) in the fluid channel 16 by the fluid sensor 10, and measurements (sensor signals) 54 correspond to measurements of the fluid with higher glycerol content (20 PG/80 VG) in the fluid channel 16 by the fluid sensor 10. Between measurements of the different fluids, the fluid channel 16 was cleaned using isopropanol and water to prevent contamination of the fluid channel 16. The measurements were delayed until the respective fluids 50, 52, 54 had filed the fluid channel 16 and a stable measurement signal could be obtained. FIG. 5 shows the measured resistance against the time.

The measurement depicted in FIG. 5 shows that the three sets of sensor signals 50, 52, 54 generated by the fluid sensor 10 based on measuring the different fluids, respectively, could clearly be distinguished from one another based upon the measured electrical resistance. It has been observed that the measured electrical resistance increased over time. Without being bound to any theory, it is believed that this increase was a result of polarization of the fluids measured with measurements 50, 52, 54. Particularly the fluid with high glycerol content, measured in measurements 54, was prone to polarization, since glycerol does not dissociate in water and so the fluid measured in measurements 54 contained a low initial ion count resulting in faster and more pronounced polarization. To avoid an increase of the measured electrical resistance over time, alternating current could be used for measuring the electrical resistance.

The example embodiments described above illustrate but are not limiting. In view of the above discussed example embodiments, some example embodiments consistent with the above example embodiments will now be apparent to one of ordinary skill in the art.

The invention claimed is:
1. A vapor-generating system, comprising:
a first fluid channel fluidly connected to a liquid source;
a pump fluidly connected to the first fluid channel and configured to deliver a liquid vapor-forming substrate from the liquid source towards a second fluid channel;

a fluid sensor, the fluid sensor configured to generate a sensor signal indicating a presence of a liquid vapor-forming substrate in the second fluid channel based on measuring an electrical property of a fluid in the second fluid channel, wherein the electrical property is an electrical resistance or dielectric constant of the fluid in the second fluid channel, wherein the sensor signal further indicates a type of liquid vapor-forming substrate in the second fluid channel based on only the electrical property of the fluid in the second fluid channel, wherein different liquid vapor-forming substrates are associated with different electrical properties, wherein the fluid sensor includes a carrier defining at least a portion of the second fluid channel between a first channel wall and a second channel wall a first electrode positioned in the carrier at the first channel wall of the second fluid channel and a second electrode positioned in the carrier at the second channel wall of the second fluid channel opposite the first electrode, a length of each of the first electrode and the second electrode extending perpendicular to the second fluid channel such that a first end of the first electrode and a first end of the second electrode are both in direct contact with the fluid in the second fluid channel;

a vaporizer configured to receive the liquid vapor-forming substrate from the fluid sensor; and a controller, the controller configured to control the vaporizer based on processing the sensor signal generated by the fluid sensor to determine which particular type of liquid vapor-forming substrate is in the second fluid channel.

2. The vapor-generating system according to claim 1, further comprising:
a dispensing device configured to dispense the liquid vapor-forming substrate, the dispensing device in fluid communication with the liquid source.

3. The vapor-generating system according to claim 2, wherein:
the second fluid channel and the fluid sensor are between the liquid source and the dispensing device; and
the fluid sensor is between the pump and the dispensing device.

4. The vapor-generating system according to claim 2, further comprising:
a main body, the main body including a power supply, wherein the liquid source, the dispensing device, the first fluid channel, the second fluid channel, and the fluid sensor are encompassed in the main body,
wherein the liquid source includes a pump and a liquid storage portion, the liquid storage portion is included in a cartridge, the cartridge configured to be releasably connected to the main body.

5. The vapor-generating system according to claim 1, wherein the fluid sensor includes a voltage divider circuit.

6. The vapor-generating system according to claim 1, wherein the liquid source includes a micropump, a micro stepper motor pump, or a piezoelectric pump.

7. The vapor-generating system according to claim 1, wherein a distance between the first end of the first electrode and the first end of the second electrode is 1 millimeter.

8. The vapor-generating system according to claim 1, wherein the first electrode and the second electrode are arranged concentrically about a common axis of the second fluid channel.

9. The vapor-generating system according to claim 1, wherein:
a second end of the first electrode opposite the first end is positioned within the carrier; and
a second end of the second electrode opposite the first end is positioned within the carrier.

10. A method for generating a vapor, the method comprising:
providing a liquid source configured to supply a liquid vapor-forming substrate;
fluidly connecting a first fluid channel to the liquid source;
coupling a pump to the first fluid channel, the pump configured to deliver the liquid vapor-forming substrate from the liquid source towards a second fluid channel;
coupling a fluid sensor to the second fluid channel, such that the fluid sensor is configured to generate a sensor signal indicating a presence of the liquid vapor-forming substrate in the second fluid channel based on measuring an electrical property of a fluid in the second fluid channel, wherein the electrical property is an electrical resistance or dielectric constant of the fluid in the second fluid channel, wherein the sensor signal further indicates a type of liquid vapor-forming substrate in the second fluid channel based only on the electrical property of the fluid in the second fluid channel, wherein different liquid vapor-forming substrates are associated with different electrical properties, wherein the fluid sensor includes a carrier defining at least a portion of the second fluid channel between a first channel wall and a second channel wall, a first electrode positioned in the carrier at the first channel wall of the second fluid channel and a second electrode positioned in the carrier at the second channel wall of the second fluid channel opposite the first electrode, a length of each of the first electrode and the second electrode extending perpendicular to the second fluid channel such that a first end of the first electrode and a first end of the second electrode are both in direct contact with the fluid in the second fluid channel; and
providing a controller, the controller configured to control a vaporizer based on processing the sensor signal generated by the fluid sensor to determine which particular type of liquid vapor-forming substrate is in the second fluid channel, the vaporizer configured to receive the liquid vapor-forming substrate from the fluid sensor.

11. The method according to claim 10, wherein the fluid sensor includes a voltage divider circuit.

* * * * *